United States Patent [19]
Bartlett et al.

[11] Patent Number: 6,160,158
[45] Date of Patent: Dec. 12, 2000

[54] FLUORINATION UTILIZING THERMODYNAMICALLY UNSTABLE FLUORIDES AND FLUORIDE SALTS THEREOF

[75] Inventors: Neil Bartlett, Orinda, Calif.; J. Marc Whalen; Lisa Chacon, both of Corning, N.Y.

[73] Assignee: The Regents of the University of California, Oakland, Calif.

[21] Appl. No.: 09/026,473

[22] Filed: Feb. 19, 1998

Related U.S. Application Data

[60] Provisional application No. 60/038,705, Feb. 20, 1997.
[51] Int. Cl.$^7$ .................................................. C07C 255/10
[52] U.S. Cl. .......................................... 558/460; 558/461
[58] Field of Search ..................................... 558/460, 461

[56] References Cited

U.S. PATENT DOCUMENTS 3,752,840  8/1973  Oxenrider et al. .................. 260/465.7

OTHER PUBLICATIONS

Zemva et al., "Thermo. Unstable Fluorides of Nickel: $NiF_4$ and $NiF_3$ Synthesis and Some Properties," *JACS*, 117, 1995, 10025–10034.

Zemva et al., "Silver Trifluoride: Preparation, Crystal Structure, Some Properties, and Comparison with $AuF_3$," *JACS*, 113, 1991, 4192–4198.

Lucier et al., "Some chemistry of high oxidation state transition metal fluorides in aHF," *J. Fluorine Chem.*, 72, 1995, 157–163.

Bartlett et al., "New fluorination of organic compounds using thermodynamically unstable nickel fluorides," *Chem. Commun.*, 1996, 1049–1050.

Whalen et al., "The Room Temperature Conversion of Nickel Difluoride to Hexafluoronickelate(IV) Salts of Alkali Cations," *J. Fluorine Chem.*, accepted for publication Sep. 5, 1997.

Whalen et al., "High–Valent Nickel Fluorides and Their Oxidizing and Florinating Properties," in "Electrochemistry in the Preparation of Fluorine and Its Compounds," Proceedings of The Electrochemical Society, vol. 97–15 (1997).

*Primary Examiner*—Joseph K. McKane
*Assistant Examiner*—Ebenezer Sackey
*Attorney, Agent, or Firm*—James M. Ritchey

[57] ABSTRACT

A method for fluorinating a carbon compound or cationic carbon compound utilizes a fluorination agent selected from thermodynamically unstable nickel fluorides and salts thereof in liquid anhydrous hydrogen fluoride. The desired carbon compound or cationic organic compound to undergo fluorination is selected and reacted with the fluorination agent by contacting the selected organic or cationic organic compound and the chosen fluorination agent in a reaction vessel for a desired reaction time period at room temperature or less.

26 Claims, 1 Drawing Sheet

FLUORINATION UTILIZING THERMODYNAMICALLY UNSTABLE FLUORIDES AND FLUORIDE SALTS THEREOF

Priority is claimed to Provisional Application No.:60/038,705, filed on Feb. 20, 1997.

The Government has rights in this invention pursuant to Contract Number DE-AC-03-76SF00098 awarded by the Director, Office of Energy Research, Office of Basic Energy Sciences, Chemical Sciences Division of the U.S. Department of Energy.

BACKGROUND OF THE INVENTION

1. Field of the Invention

Fluorination of perhydro carbon containing materials is achieved under mild temperature conditions to yield useful perfluoro derivatives. More specifically, perhydro organic compounds and organic cations are converted to their perfluoro relatives by treatment with thermodynamically unstable fluorine containing compounds (such as $NiF_3$ and $NiF_4$) and fluorine containing salts (such as salts containing $NiF_6^{2-}$).

2. Description of the Background Art

An important industrial process for the conversion of organic precursors to fully fluorinated derivatives (perfluoro carbon compounds) is the Simons Process. The Simons Process (J. H. Simons, *J. Electrochem. Soc.*, 95, 1949, 47; J. H., Simons, H. T. Francis and J. A. Hogg, ibid., 95, 1949, 53; J. H. Simons and W. J. Harland, ibid., 95, 1949, 55; J. H. Simons, W. H. Pearlson, T. J. Briace, W. A. Wilson and R. D. Dresdner, ibid., 95, 1949, 59; J. H. Simons and R. D. Dresdner, ibid., 95, 1949, 64, J. H. Simons (ed.), in *Fluorine Chemistry*, Vol. 1, Academic, New York, 1950, p. 414; J. H. Simons and T. J. Brice, ibid., Vol. 2, 1954, p. 333, J. Burdon and J. C. Tatlow, *Adv. Fluorine Chem.*, 1, 1960, 129, and S. Nagase, *Fluorine Chem. Rev.*, 1, 1967, 77, all of which are herein incorporated by reference) uses an electrochemical cell to oxidize perhydro-organic materials, at a nickel anode, to their perfluoro-relatives. The electrolyte for that process is liquid anhydrous hydrogen fluoride (aHF) in which sodium fluoride, or other fluorobases, are dissolved (the latter, to provide for electrical conductance).

Thus, at this time, the bulk of perfluoro-organic materials (other than perfluoro-polymers such as Teflon) are made by adaptions of the Simons electrochemical fluorination (ECF) process in which organic compounds are electrochemically oxidized and fluorinated at a nickel anode in aHF, made conducting with a weak base.

Subject Applicants have demonstrated (N. Bartlett, R. D. Chambers, A. J. Roche R. C. H. Spink, L. Chacón, and J. M. Whalen, *Chem. Commun.*, 1996, 1049, which is herein incorporated by reference) that the Simons Process chemistry could be conveniently simulated at room temperature, and often in high efficiency using nickel trifluoride ($NiF_3$), nickel tetrafluoride ($NiF_4$) or hexafluoronickelate(IV) salts. The thermodynamically unstable fluorides, $NiF_3$ and $NiF_4$, were first established by Applicant Bartlett and his collaborators (B. Zemva, K. Lutar, L. Chacón, M. Fele-Beuermann, J., Allman, C. Shen, and N. Bartlett, *J. Am. Chem. Soc.*, 117, 1995, 10025, Which is herein incorporated by reference), the precursor from which both are derived being the commercially available salt potassium hexafluoronickelate (IV), $K_2NiF_6$. The latter is prepared by an adaption of the original synthesis of Klemm and Huss (W. Klemm, and E. Huss, *Z. anorg. Chem.*, 258, 1949, 221, which is herein incorporated by reference), in which nickel (II) chloride and potassium fluoride are heated in a nickel bomb with fluorine gas under pressure (several atmos.) at 275° C.

Fluorocarbon compounds can often be derived from hydrocarbon precursors by well controlled interaction of the latter with elemental fluorine, as pioneered by Margrave and Lagow, (J. L. Margrave and R. J. Lagow, *Prog. Inorg. Chem.*, 26, 1979, 161, and references therein, which are herein incorporated by reference) and Lagow and his co-workers. (R. J. Lagow, T. R. Bierschenk, T. J. Juhlke, and H. Kawa, in *Synthetic Fluorine Chemistry*, ed. G. A. Olah, R. D. Chambers, and G. K. S. Prakash, J. Wiley, New York, 1972, ch. 5, p. 97 and references therein, which are herein incorporated by reference). This previous method also requires precise control of $F_2$ gas pressures and substrate concentrations. Although the convenient reagent cobalt trifluoride, $CoF_3$, is less potent than elemental fluorine, it has long been employed in the synthesis of highly fluorinated organic compounds (M. Stacey and J. C. Tatlow, *Adv. Fluorine Chem.*, 1060, 1, 166 and references cited therein; R. E. Banks and J. C. Tatlow, *Fluorine, the First Hundred Years*, ed. R. E. Banks, D. W. A Sharpe and J. C. Tatlow, Elsevier, 1986, p. 267, 337, and references cited therein, both of which are herein incorporated by reference). Nevertheless, high temperatures are necessary for the process, depending on the substrate, and this has often resulted in unwanted carbon-carbon bond cleavage. The use of the subject $NiF_3$, $NiF_4$ or $NiF_6^{2-}$ species provides for easy control of the fluorination process, as in the Simons Process, but without the awkward experimental aspects of the latter. Those awkward aspects arise from the requirement, that the substrate to be fluorinated, has to be carried effectively to the surface of a nickel anode of the electrochemical cell, and the products separated from the effluent gases, which have come from that anode.

It is noted that the conversion of $NiF_2$ to $NiF_6^{2-}$ has been previously achieved at ordinary temperatures but only with the exotic reagent krypton difluoride (A. Jesih, K. Lutar, I. Leban, and B. Zemva, *Inorg. Chem.*, 28, 1989, 2911, which is herein incorporated by reference), which is itself a costly material to prepare, and dangerous to use (because of its thermodynamic instability) in quantities of more than a few grams. The novel subject method provides an effective conversion of $NiF_2$ to $NiF_6^{2-}$ which uses no more than one atmosphere pressure of elemental fluorine, and temperature of 0° C. to room temperature. Since $NiF_2$ is insoluble in aHF, and the $NiF_6^{2-}$ salts of the alkalis are all soluble, the latter are readily separated from the former.

It is further noted that presently $NiF_6^{2-}$ salts are made by adaptions of the original synthesis (W. Klemm, and E. Huss, *Z. anorg. Chem.*, 258, 1949, 221) of Klemm and Huss. For small scale high purity synthesis of more exotic salts such as $(XeF_5)_2NiF_6$, krypton difluoride has been used (A. Jesih, K. Lutar, I. Leban, and B. Zemva, *Inorg. Chem.*, 28, 1989, 2911). the former synthesis is inefficient with $NiF_2$ as the nickel reagent, the latter is costly, and, on a large scale, potentially dangerous. Neither synthesis competes in effectiveness with that described here for $NiF_6^{2-}$ salt synthesis from $NiF_2$.

It is additionally noted, therefore, that anyone currently wishing to convert $NiF_2$ to $NiF_6^{2-}$ salts would use either the thermal method of Klemm and Huss (W. Klemm, and E. Huss, *Z. anorg. Chem.*, 258, 1949, 221) or resort to using krypton difluoride (A. Jesih, K. Lutar, I. Leban, and B. Zemva, *Inorg. Chem.*, 28, 1989, 2911). The former method is not effective for the synthesis of $Li_2NiF_6$, and the other alkali salts would be highly impure unless the mixture of $NiF_2$ and alkali fluoride was reground and refired several times. The synthesis of krypton difluoride and the handling of that reagent is only practiced in a limited number of laboratories world-wide, whereas the subject process described here for $NiF_2$ conversion to $NiF_6^{2-}$, could be readily adopted by any laboratory accustomed to the handling of aHF and $F_2$.

The foregoing information reflects the state of the art of which the applicant is aware. in relation to the subject invention, and is tendered with the view toward discharging applicant's acknowledged duty of candor in disclosing information which may be pertinent in the examination of this application. It is respectfully submitted, however, that any disclosed, non-subject matter information does not teach or render obvious applicant's claimed invention.

SUMMARY OF THE INVENTION

At the centennial celebrations for the discovery of Fluorine (that were held in Paris in June 1986) as a result of hearing a talk given by K. O. Christe, one of the subject Applicants (Neil Bartlett) got an idea. That idea was to prepare thermodynamically unstable fluorides (such as silver trifluoride, $AgF_3$, and nickel tetrafluoride, $NiF_4$,) by taking fluoride ion from the known anions ($AgF_4^-$, and $NiF_6^{2-}$) using strong $F^-$ acceptors, such as boron trifluoride, $BF_3$, in anhydrous liquid hydrogen fluoride (aHF). This idea worked and resulted in the publications "Thermodynamically Unstable Fluorides of Nickel: $NiF_4$ and $NiF_3$ Syntheses and Some Properties" *J. Amer. Chem. Soc.*, 117, 1995, 10025 and "Silver Trifluoride: Preparation, Crystal Structure, Some Properties, and Comparison with $AuF_3$", *J. Amer. Chem. Soc.*, 113, 1991, 4192.

As the chemical properties of these thermodynamically unstable fluorides were discovered, Applicant Bartlett realized that their oxidizing properties were commonly associated with the capture of electrons from the substrate that was oxidized. Unambiguous cases of this are the oxidation of oxygen, $O_2$, to $O_2^+$, and the oxidation of xenon, Xe. Applicant Bartlett also concluded that a similar electron oxidation also initiated the observed fluorination of perfluoropropene by each of the new fluorides. Applicant Bartlett had long been aware of the Simons electrochemical fluorination method (ECF) for the fluorination of organic materials to their perfluoro-relatives at a nickel anode. He was also aware, that from early days of the demonstrated effectiveness of this process, that the intermediacy of higher nickel fluorides had been suspected, but only suspected. This led Applicant Bartlett to postulate that the new nickel fluorides would bring about the same sort of fluorinations as the Simons ECF process. In addition he considered that the ECF process probably also proceeded by a primary step involving electron oxidation. What Applicant Bartlett recognized, also, was that for many costly organic materials, the use of the nickel fluorides (which are themselves insoluble in aHF) in the low boiling, easily recovered solvent aHF, could provide a simple clean alternative to ECF. As documented thoroughly below, the fluorination effectiveness of the nickel fluorides on a set of well chosen organic molecules has been confirmed and shown.

The subject approach, by using the required quantity of oxidant, in a one-container procedure, generates the perfluorinated compound free of underfluorinated products, and in essentially a quantitative yield which is a great advantage over the ECF method. The reduction product in the novel subject approach is nickel difluoride ($NiF_2$). In addition, alkali-hydrofluoride (AF.xHF) and alkali fluoroborate ($ABF_4$) remain, when the perfluorinated product and aHF have been removed. By simply heating this residue, $BF_3$ is recovered from the $ABF_4$ (A=Li is best), and the resulting mixture of AF and $NiF_2$, with added elemental fluorine ($F_2$) in the (recovered) aHF, is then converted back to the $A_2NiF_6$ salt, using light to photo-dissociate the $F_2$ (visible light is suitable, but microwave energy could also be applied). The subject approach is particularly attractive for the fluorination of costly, low-volatility, and low solubility (in aHF) organic compounds. For such materials, the new approach provides efficient fluorination via the aHF solution of the $NiF_6^{2-}$, which effectively carries the oxidizer to the insoluble organic substance,(which, as it fluorinates, becomes more soluble in the aHF). For such insolubles, the ECF approach is ineffective.

Therefore, with the above preface and following descriptive material in mind, an object of the present invention is to provide a method for the conversion of perhydro carbon compounds, including hydrocarbons, ethers, ketones, alcohols, esters, nitriles, and unsaturated compounds to their perfluoro relatives.

Another object of the present invention is to furnish a method for the conversion of borohydride anions (e.g., $B_nH_n^{2-}$ salts) carboborohydride anions (e.g., $CB_{n-1}H_n$) and dicarboranes (e.g., $C_2B_{n-2}H_n$) to their perfluoro relatives ($B_nF_n^{2-}$, $CB_{n-1}F_n^{31}$, $C_2B_{n-2}F_n$).

A further object of the present invention is to relate a method for deriving $NiF_4$ and $NiF_3$ from the $NiF_6^{2-}$ salts which permits provision of elemental fluorine for any fluorination reaction in a manner that can be regulated by controlling the supply of boron trifluoride (or other fluoride-ion acceptor) to the $NiF_6^{2-}$ salt dissolved in aHF (anhydrous HF).

Still another object of the present invention is to disclose that salts of $NiF_6^{2-}$ dissolved in aHF are effective in direct substitution of fluorine for hydrogen ligands in cationic species.

Still yet another object of the present invention is to present a method that allows a combination of $NiF_6^{2-}$ salts and ECF fluorination procedures to dispense with the need for the binary fluorides and hence dispense with any need for $BF_3$.

Still yet an additional object of the present invention is to provide a method for fluorination of organic compounds and organic cations with nickel containing fluorides and nickel containing fluoride salts.

Generally, disclosed is a method in which hydrogen in organic compounds is substituted by fluorine in simply controlled reactions, at or below room temperatures. The reactions are done in liquid anhydrous hydrogen fluoride (aHF) which is easily and quantitatively recovered. Most of the hydrogen in an organic molecule is replaced quickly and cleanly by simply using a solution of a $NiF_6^{2-}$ salt for the oxidation. Hydrogen at tertiary carbon sites in highly fluorinated materials require, for their oxidation, the binary fluorides $NiF_4$ or $NiF_3$ that are simply produced from the $NiF_6^{2-}$ salt by adding gaseous boron trifluoride ($BF_3$) to the aHF solution.

Clearly, the subject process could supplement the ECF method even for bulk chemical production. There would be plain advantages to those skilled in the art to use $NiF_6^{2-}$ salts in aHF to bring about the greater part of the F for H substitution. The fluorination would then be completed using ECF (F for the tertiary H) on the more aHF soluble material and thus avoiding use of $BF_3$. For high-cost organic compounds, and especially those with low solubility in aHF, the new approach is, most likely, the only viable one.

More specifically, disclosed herein are hexafluoronickelate (IV) salts (containing $NiF_6^{2-}$) and the thermodynamically unstable fluorides $NiF_4$, $NiF_3$, and $NiF_x$, (wherein: $2<x<3$) (all derived from $NiF_6^{2-}$ salts) are used as fluorinating agents. Hexafluoronickelate salts, $NiF_6^{2-}$, that are soluble in liquid anhydrous hydrogen fluoride are the least powerful of these oxidizers, but they are valuable for the first and most energy releasing steps in a fluorination process, especially I the conversion of perhydro carbon compounds to perfluoro relatives.

The $NiF_6^{2-}$ salts convert hydrogen ligands on carbon to fluorine ligands except for hydrogen on a tertiary carbon atom, that tertiary carbon being linked to three other atoms, each carrying fluorine ligands. For the conversion of such tertiary carbons hydrogen ligands to fluorine ligands, the more powerful oxidizers $NiF_4$ or $NiF_3$ are required.

The most powerful oxidizers and fluorinators, $NiF_4$ and $NiF_3$, are generated, in situ, from $NiF_6^{2-}$ (the latter in solution in aHF) by adding a fluoride-ion acceptor, such as $BF_3$, to the solution. The aHF solvent acts as a barrier between the aHF insoluble $NiF_4$ and $NiF_3$, and the materials that are to be fluorinated. The latter diffuse or are stirred across this barrier, at a suitable rate for their controlled fluorination. Greatest efficiency of conversion, with least destruction of the substrate molecular framework, is achieved by first fluorinating with $NiF_6^{2-}$ (in aHF), the fluorination being completed by forming $NiF_4$ in situ, in the same container.

In the case of the unsaturated hydrocarbon systems and other highly reducing substrates, they can be first converted to saturated, or less reducing systems by initial treatment with salts of $NiF_6^{2-}$ in aHF or cobalt trifluoride. (Cobalt trifluoride and its reduction product cobalt difluoride are each insoluble in aHF). The partially fluorinated product (e.g., a saturated fluorohydrocarbon) can then be transferred, in aHF, ior $NiF_6^{2-}$ or $NiF_4$ or $NiF_3$ treatment, as appropriate.

Low temperature fluorinations (down to -78° C.) can be easily achieved in these aHF-based systems. Low temperature, and high dilution in the case of the $NiF_6^{2-}$ fluorinations, can minimize substrate molecular framework attack. This is important for the preservation of the molecular integrity of highly reducing substrates such as olefins, acetylene, and the like.

Elemental fluorine does not usually attack cations, but $NiF_6^{2-}$ (used in solution of its salts in aHF) do so with high efficiency, when the $NiF_6^{2-}$ oxidizer is introduced, with good mixing, into a solution of the salt, the cation of which is to be fluorinated. An illustrative example is the fluorination of tetramethylammonium cation, $(CH_3)_4N^+$, to the new species tetrakis-difluoromethylammonium cation, $[(CF_2H)_3NCH_3]^+$, in better than 70% yield, using an $NiF_6^{2-}$ salt in aHF below -30° C.

When the subject $NiF_3$ or $NiF_4$ (the latter prepared from $K_2NiF_6$ in situ) are used to fluorinate organic compounds, the solvent (as in the Simons Process) is liquid anhydrous hydrogen fluoride and this serves to carry even slightly soluble organic precursors to the insoluble $NiF_3$ or $NiF_4$, where the organic compounds are efficiently fluorinated, at room temperature or below. In these fluorination reactions the subject $NiF_3$, $NiF_4$, or $NiF_6^{2-}$ are reduced to $NiF_2$ (which is also insoluble in aHF). Since the subject $NiF_3$ and $NiF_4$ are thermodynamically unstable with respect to $NiF_2$ and elemental fluorine ($F_2$), they cannot be remade by simply exposing $NiF_2$ to $F_2$. Their resynthesis depends upon the conversion of $NiF_2$ to a hexafluoronickelate salt $NiF_6^{2-}$, from which they can again be derived.

For the subject $NiF_3$, $NiF_4$ or $NiF_6^{2-}$ fluorinators to be competitive with the Simons Process, it was necessary to find a simple way to regenerate the subject $NiF_6^{2-}$ from the $NiF_2$; the latter produced when these oxidizers fluorinate the organic substrates. An effective means of bringing about that conversion of $NiF_2$ to $NiF_6^{2-}$ has now been found.

The conversion of $NiF_2$ to a subject $NiF_6^{2-}$ salt requires atomic fluorine and a highly basic environment (high effective $F^-$ concentration) in order to excite the Ni(IV) oxidation state. The higher-temperature ($\geq 275°$ C.) traditional batch syntheses, in nickel or Monel pressure reactors, meet these requirements, but because of the solid-state nature of the reactants and product, the latter is never of high purity in one firing.

The conversion of $NiF_2$ to the subject $NiF_6^{2-}$ disclosed here uses light to generate fluorine atoms from molecular fluorine. In addition, the solvent aHF, which dissolves alkali hydrofluoride, and their $NiF_6^{2-}$ salts, thus provides the strongly basic environment necessary for the formation of $NiF_6^{2-}$. Translucent fluorocarbon polymer tubing (FEP) is a kinetically inert container material that transmits the light effectively to the solution of alkali fluoride and fluorine in the aHF. The conversion proceeds effectively at room temperatures.

Other objects, advantages, and novel features of the present invention will become apparent from the detailed description that follows, when considered in conjunction with the associated drawings.

DESCRIPTION OF THE PREFERRED EMBODIMENT

Figure 1:
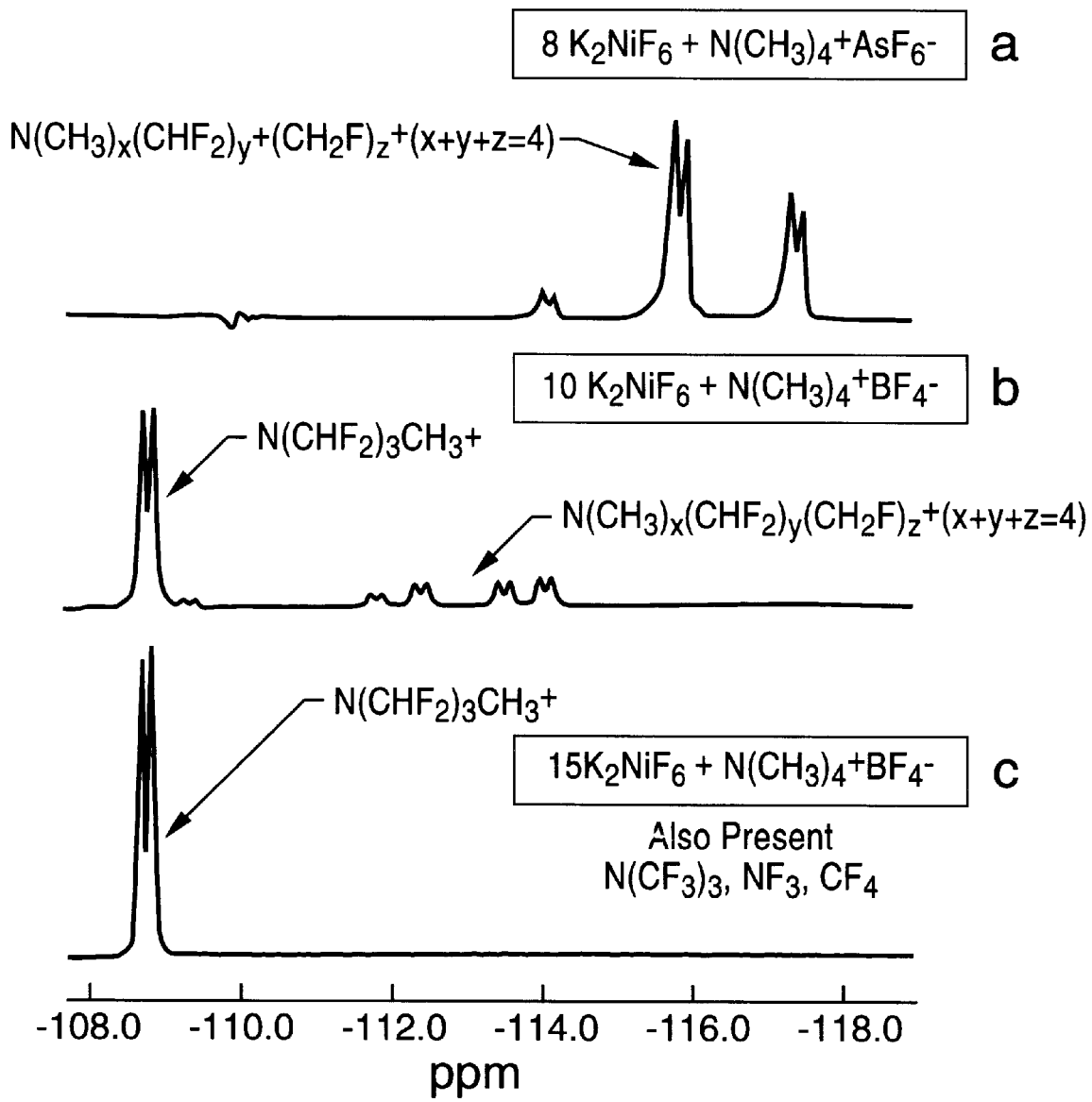
FIG. 1a is a $^{19}F$ NMR spectrum for the products of a $K_2NiF_6$ interaction with $N(CH_3)_4^+AsF_6^-$ in aHF for an 8:1 ratio, respectively.
FIG. 1b is a $^{19}F$ NMR spectrum for the products of a $K_2NiF_6$ interaction with $N(CH_3)_4^+BF_4^-$ in aHF for a 10:1 ratio, respectively.
FIG. 1c is a $^{19}F$ NMR spectrum for the products of a $K_2NiF_6$ interaction with $N(CH_3)_4^+BF_4^-$ in aHF for a 15:1 ratio, respectively.

In general, the subject invention discloses that replacement of hydrogen by fluorine in a variety of organic compounds and cationic species is accomplished with high efficiency in liquid hydrogen fluoride (aHF), at or below 20° C., using the thermodynamically unstable fluorides $NiF_3$, $NiF_4$, (the latter prepared in situ from $K_2NiF_6$ with $BF_3$), and $NiF_6^{2-}$.

For fluorination via the Simons electrochemical cell (as cited above and in Y. W. Alsmeyer, W. V. Childs, R. M. Flynn, G. G. I. Moore, and J. C. Smeltzer, *Organofluorine Chemistry*, ed. R. E. Banks, B. E. Smart, and J. C. Tatlow, Plenum Press, 1994, ch.5, p.121 and references cited therein and herein incorporated by reference) it is conjectured that higher fluorides of nickel are formed at the anode in this process. The Simons process evidently requires lower activation temperatures than $CoF_3$, but this route to highly fluorinated organic compounds has generally been most effective with precursors that are soluble in aHF. The recent preparation of the thermodynamically unstable nickel fluorides $NiF_3$ and $NiF_4$, and the demonstration that the latter quantitatively fluorinates perfluoropropene to perfluoropropane below room temperature (B. Zemva, K. Lutar, L. Chacon, M. Fele-Beuermann, J. Allman, C. Shen, and N. Bartlett,

*J. Amer. Chem. Soc.*, 1995, 117, 10025, which is herein incorporated by reference), indicates that this reagent is a more easily applied fluorinator than either $CoF_3$ or the Simons process, for the preparation of highly fluorinated organic compounds. Since $K_2NiF_6$ is readily available, and the more potent oxidizers $NiF_4$ and $NiF_3$ are conveniently prepared from this reagent in aHF, all three of these materials were studied in interaction with a variety of organic substrates, using experimental techniques described previously (B. Zemva, K. Lutar, L. Chacón, M. Fele-Beuermann, J. Allman, C. Shen, and N. Bartlett, *J. Amer. Chem. Soc.*, 1995, 117, 10025, which is herein incorporated by reference) (i.e. all manipulations and reactions were performed using transparent fluorocarbon tubing).

To reduce to practice the subject systems, Applicants utilized model compound 1 that had been shown previously to be very efficiently fluorinated by both $CoF_3$ (R. D. Chambers, B. Grievson, F. G. Drakesmith, and R. L. Powell, *J. Fluorine Chem.*, 1985, 29, 323, which is herein incorporated by reference) and the Simons cell process (R. D. Chambers, R. W. Fuss, and M. Jones, *J. Fluorine Chem.*, 49, 1990, 409, which is herein incorporated by reference). We have now established that this cyclic ether (which like many oxygen containing species is moderately soluble in aHF) is efficiently fluorinated by R-$NiF_3$ ($NiF_3$ has been shown to exist in at least three forms: approximately hexagonal-close-packed rhombohedral (R-$NiF_3$), hexagonal tungsten bronze (H-$NiF_3$) and pyrochlore (P-$NiF_3$) (B. Zemva, K. Lutar, L. Chacón, M. Fele-Beuermann, J. Allman, C. Shen, and N. Bartlett, *J. Am. Chem. Soc.*, 117, 1995, 10025)) at or below, room temperature, to give perfluorinated compound 1a. Interaction of MeCOF with R-$NiF_3$ was also of interest since this molecule is efficiently perfluorinated in the Simons process. Although $CF_3COF$ was seen to be formed below 0° C., further fluorination to the highly volatile products $CF_4$ and $COF_2$ easily occurred, and yields of $CF_3COF$ were always low. This indicates that the nickel fluoride formed at the Simons process anode is a less powerful fluorinator than R-$NiF_3$.

Scheme 1.
Reagents and conditions; I, R-$NiF_3$,
aHF (initiated at -28° C. <T<-20° C. for 2.5 h), 24h.

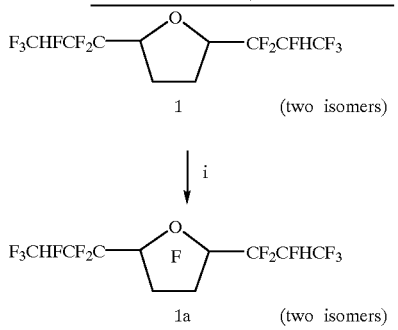

The oxidative potency of R-$NiF_3$ is illustrated by its facile oxidation of MeCN, which is resistant to strong oxidizers (A. A. A. Emara and G. J. Schrobilgen, *J. Chem. Soc. Chem. Commun.*, 1987, 1644, which is herein incorporated by reference). When the initial interaction with MeCN in aHF was at -20° C. to -25° C. (3 h), the carbon-nitrogen bond cleavage was minimal and $CF_3CN$ the major product, but when the interaction was -15° C. to -20° C., $C_2F_6$ and $NF_3$ were the major products. $K_2NiF_6$ (in solution in aHF) with MeCN, initiated at -20° C. to -25° C. proved to be the best perfluorination reagent for MeCN, giving $CF_3CF_2NF_2$ and $CF_3CN$ (2:1), with $C_2F_6$, $NF_3$, and $CF_4$ as minor products (ca. 1–2% each). The Simons process also yields $CF_3CN$ and $CF_3CF_2NF_2$ with maximum current efficiencies of 40% and 8%, respectively (N. Watanabe and M. Haruta, *Kenkyu Hokoku Asahi Garasu Kogyo Gitjutsu Shoreikai*, 1975/76, 27, 1; 1974, 25, 11 which is herein incorporated by reference).

The Simons process is much less useful, in general, for the fluorination of compounds which have a low solubility in aHF. Precursor 2, was selected for the examination of the metal fluoride fluorinations for this reason and also because the fluorination of these cyclohexyl derivatives in vapor phase fluorinations over $CoF_3$, always undergo some fragmentation. In addition, 2 has tertiary carbon-hydrogen bonds which are much more difficult to substitute with fluorine than the hydrogen ligands of a $CH_2$ group. Separate interactions of 2 with R-$NiF_3$, $NiF_4$, and $K_2NiF_6$ were carried out to probe their relative effectiveness in carrying through the fluorination. Although R-$NiF_3$ in interaction with 2 in aHF at 20° C. gave largely the perfluorinated product 2a, this compound can also be produced more easily and with even less contamination, by the in situ generation of $NiF_4$ from $K_2NiF_6$ with $BF_3$ below 0° C. When a solution of $K_2NiF_6$ in aHF was added to an aHF solution of 2 at 0° C., the rapid precipitation of a red-brown lower fluoride of nickel (B. Zemva, K. Lutar, L. Chacón, M. Fele-Beuermann, J. Allman, C. Shen, and N. Bartlett, *J. Amer. Chem. Soc.*, 1995, 117, 10025, both of which are herein incorporated by reference) indicated that fluorination of 2 had occurred, and $^{19}F$ NMR and GLCMS confirmed the product to be 2b. This indicates that the more readily replaceable protons in organic compounds can probably be exchanged for fluorine by aHF solutions of the commercially available $K_2NiF_6$ at ordinary temperatures. When tertiary protons, or other less labile hydrogen ligands need to be substituted, the greater fluorinating power of $NiF_4$ can then be provided by the addition of $BF_3$.

Scheme 2.
Reagents and conditions; i, R-$NiF_3$,
aHF, 0° C., 24 h; ii, $NiF_4$
(generated in situ), aHF, 0° C., 24 h;
iii, $K_2NiF_6$, aHF, 20° C., 24h.

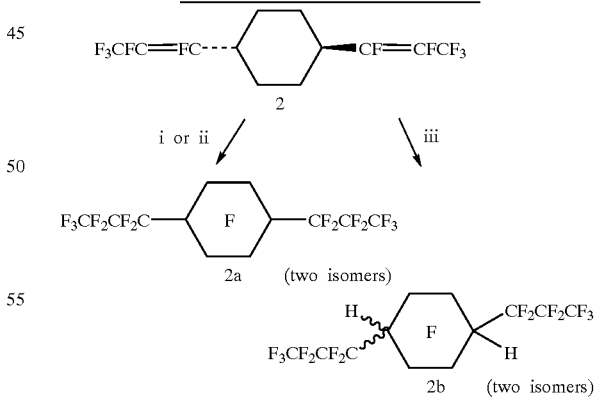

Previous work in the laboratory of R. D. Chambers had attempted the vapor phase fluorination over $CoF_3$ of the adamantane derivative 3, to yield the desired product 3a. However, fragmentation dominated, and 3a was never observed. However, with either R-$NiF_3$ or $NiF_4$ (generated in situ) at 20° C. or below, the fluorination of 3 proceeded efficiently to give 3a, with no other significant product observed. In contrast, $K_2NiF_6$ with 3, did not act as a fluorinator.

Scheme 3.
Reagents and conditions; i, $NiF_4$
(generated in situ), aHF, 20° C., 24 h.

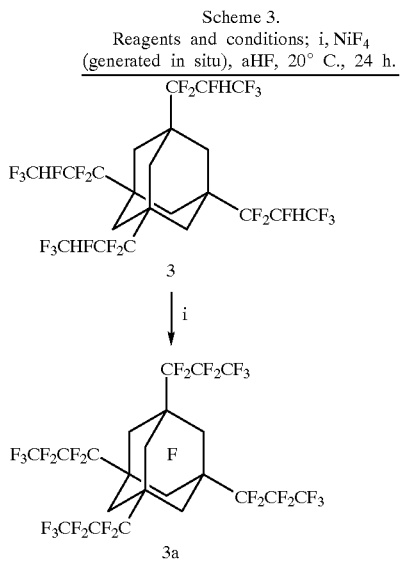

Thus, the subject invention comprises a new approach to the synthesis of highly Fluorinated compounds, that proceeds remarkably efficiently at room temperature or below. For reaction schemes of 1, 2, and 3 no significant other products were present, providing that an excess of fluorinating agent was used.

Even though $NiF_4$ and $NiF_3$, each thermodynamically unstable (with respect to loss of $F_2$ and $NiF_2$), are preparable (B. Zemva, K. Lutar, L. Chacón, M. Fele-Beuermann, J. Allman, C. Shen, and N. Bartlett, *J. Amer. Chem. Soc.*, 117, 1995, 10025) from $NiF_6^{2-}$ salts (W. Klemm, and E. Huss, *Z. Anorg. Chem.*, 258, 1949, 221) and can be used in aHF as oxidizing and fluorinating agents (N. Bartlett, R. D. Chambers, A. J. Roche, R. C. H. Spink, L. Chacón, and J. M. Whalen, *Chem. Commun.*, 1996, 1049), $NiF_4$ and $NiF_3$ can be prepared and used in situ of the substrates to be oxidized and fluorinated, a convenient method being via the introduction of boron trifluoride:

$$2BF_3+NiF_6^{2-} \rightarrow 2BF_4^- +NiF_4 \qquad (1)$$

$NiF_4$ converts to $NiF_3$ above −60° C. and rapidly at 0° C.:

$$NiF_4 \rightarrow NiF_3 + \tfrac{1}{2}F_2 \qquad (2)$$

$NiF_3$ can be kept indefinitely as a dry black solid at ~20° C. or below, but slowly falls to $NiF_2$ and $F_2$ in aHF at ~20° C. $NiF_3$, is insoluble in aHF, but this solvent provides an excellent medium for the transport of compounds to be fluorinated by this fluoride. Many of the fluorination reactions, particularly with perhydro carbon compounds can be carried out with high efficiency in this solvent at temperatures well below 0° C. Fluorination by $NiF_3$ resembles electrochemical fluorination at a nickel anode. Although the conversion of $CH_3COF$ to $CF_3COF$ is of low efficiency because of the facile formation of $COF_2$, many larger and less easily cleaved molecules (including substituted adamantanes shown in Scheme 3 above (N. Bartlett, R. D. Chambers, A. J. Roche, R. C. H. Spink, L. Chacón, and J. M. Whalen, *Chem. Commun.*, 1996, 1049)) can be efficiently converted to their perfluoro relatives. The oxidizing potency of the $NiF_3$ is illustrated by the conversion of $CH_3CN$ to $CF_3CN$, $CF_3CF_2NF_2$ and other products well below 0° C.

Because of the solvolytic instability of the $NiF_6^{3-}$ ion in aHF, and the release of base, $\{F(HF)_x^-\}$, salts of this ion produce $NiF_6^{2-}$, and an ill defined red $NiF_x$ (3>x>2). $NiF_6^{3-}$ salts are therefore less powerful oxidizers than $NiF_3$ but are sometimes (as in the formation of $CF_3CF_2NF_2$ from $CH_3CN$) more effective in generating an uncleaved perfluoro product.

As stressed previously, the subject $NiF_6^{2-}$ salts in aHF are convenient fluorinators and will commonly replace protons on carbon with fluorine, except when the proton is associated with a tertiary carbon, already linked to three perfluoronated carbon centers. For that replacement, $NiF_3$ is required. The $NiF_6^{2-}$ salts provide the advantage that they are soluble in aHF. Substrates to be fluorinated can be titrated to an end-point of persistent color of $NiF_6^{2-}$ in the aHF (red), signaling the completion of the oxidation. Fluorination resistant centers can be subsequently oxidized with $NiF_3$ or by ECF.

A particular advantage of $NiF_6^{2-}$ as a fluorinating and oxidizing agent derives from its anionic nature. The interaction with the $N(CH_3)_4^+$ species is an instance of this. This generates the novel cation $[(CF_2H_3)NCH_3]^+$ in greater than a 70% yield when the reaction is carried out at −70° C. Oxidation of $N(CH_3)_4^+$ or $N(CH_3)_3$ with $NiF_3$ gives largely $N(CF_3)_3$.

The regeneration of $NiF_6^{2-}$ from $NiF_2$ (the common reduction product of $NiF_4$, $NiF_3$ and $NiF_6^{2-}$) is easily achieved applying Applicants' invention by using F atoms (generated by sunlight or UV light) from $F_2$ in aHF containing alkali fluoride at ~20° C.:

$$NiF_2+2\{F(HF)^-_x\}+2F^- \rightarrow NiF_6^{2-}+2xHF \qquad (3)$$

The most convenient alkali fluoride is LiF, since $Li_2NiF_6$ is of low solubility in aHF relative to LiF, a large molar excess of the latter both enhancing the rate of formation of the $NiF_6^{2-}$ and decreasing the solubility of $Li_2NiF_6$ by mass action.

As noted above, $NiF_2$ is oxidized, at ~20° C., to $NiF_6^{2-}$ by sunlight or ultraviolet light irradiated $F_2$ in liquid anhydrous hydrogen fluoride (aHF) containing alkali fluoride. Quantitative formation of $NiF_6^{2-}$ can be achieved with strongly basic solutions (e.g. KF: HF molar ratio ~1:4). $Li_2NiF_6$, which was previously unknown, is the least aHF soluble of the alkali salts, and can be easily prepared in high purity.

When $NiF_3$ or $NiF_4$ (the latter prepared from $K_2NiF_6$ in situ (potassium hexafluoronickelate(IV), $K_2NiF_6$, is a commercially available salt prepared by an adaption of the original synthesis of Klemm and Huss (W. Klemm, and E. Huss, *Z. anorg. Chem.*, 258, 1949, 221)) are used to fluorinate organic compounds, the solvent is aHF and this serves to carry even slightly soluble organic precursors to the insoluble $NiF_3$ or $NiF_4$, where the organic compounds are efficiently fluorinated, at room temperature or below. In these fluorination reactions the $NiF_3$ and $NiF_4$ are reduced to $NiF_2$ (which is also insoluble in aHF). Since $NiF_3$ and $NiF_4$ are thermodynamically unstable with respect to $NiF_2$ and elemental fluorine ($F_2$), they cannot be remade by simply exposing $NiF_2$ to $F_2$. Their resynthesis depend upon the conversion of $NiF_2$ to a salt of hexafluoronickelate (IV), ion $NiF_6^{2-}$, from which they can be derived.

For the $NiF_3$, $NiF_4$, or $NiF_6^{2-}$ fluorinators to be competitive with the Simons Process, it was necessary to find a simple way to regenerate $NiF_6^{2-}$ from the $NiF_2$; the latter produced when these oxidizers fluorinate the organic substrates. A process for the conversion of $NiF_2$ to $NiF_6^{2-}$, at room temperature, has now been found and is herein described. The conversion is especially effective in the production of the new salt, $Li_2NiF_6$, which is made in high purity.

The effectiveness of the conversion of the aHF—insoluble $NiF_2$ to $NiF_6^{2-}$ in the subject light-promoted fluorinations, in aHF made basic with alkali fluoride, is remarkably high. Photodissociation of $F_2$ to $F^\cdot$ atoms must be the consequence of absorption of the relatively high-energy photons associated with $F_2$ light absorption, the maximum of which is close to 3000 Å, (but with a broad tail into the visible). As is well known (G. Herzberg, "Spectra of Diatomic Molecules" D. Van Nostrand Co., Inc., New York, 1964, pp 389–390, which is herein incorporated by reference) this absorption has no band structure, the continuum character signifying that the absorption is associated with electron promotion from the bonding levels to the σ* orbital, and hence, dissociation to atoms (A. L. G, Rees, *J. Chem. Phys.*, 26, 1957, 1567, which is herein incorporated by reference). The F—atom effective lifetime could be augmented by the formation of species such as $F_2^{\cdot -}$, or its hydrogen bonded solvates $(F_2^\cdot HF)^-$ or $(F_2^\cdot 2HF)^-$, in the strongly basic aHF. The high effectiveness of strongly basic aHF solutions in generating $NiF_6^{2-}$ could be a consequence of that augmentation (compare the results of row 7 with those of row 8, Table 3 and note the 100% yield for row 4). The charged $F_2^{\cdot -}(g)$ (or its HF solvates), unlike neutral $F^\cdot$ cannot quickly regenerate $F_2$. Since the electron affinity of $F_{(g)}$ is 3.399 eV (H. Hotop, and W. C. Lineberger, *J. Phys. Chem. Ref. Data*, 4, 1975, 539, which is herein incorporated by reference) and that of $F_{2(g)}$ is 3.10 eV (B. K. Janousek, and J. I Brauman, in "Gas Phase Ion Chemistry", M. T. Bowers, ed., vol 2, chapter 10, p. 53, Academic, New York, 1979, which is herein incorporated by reference) the $F_2^{\cdot -}$ species must be less bound than $F_{2(g)}$ by 0.299 eV, therefore this, or its HF solvates, should be more effective fluorine atom sources than $F_2$ itself. In addition, and in contrast to $F^\cdot$ and $F_2$, such $F_2^{\cdot -}$ species would also be nucleophilic. In the syntheses carried out in sunlight, it was observed that the particles of the aHF—insoluble pale yellow-green $NiF_2$ became black, before any coloring of the aHF solution occurred. This suggests that the $NiF_2$ is first fluorinated to $NiF_3$, that fluoride then interacting slowly with the solvated $F^-$ to generate $NiF_6^{2-}$ by disproportionation, as previously described (B. Zemva, K. Lutar, L. Chacón, M. Fele-Beuermann, J. Allman, C. Shen, and N. Bartlett, *J. Am. Chem. Soc.*, 117, 1995 10025):

$$2NiF_{3(c)} + 2F^-_{(solv)} \rightarrow NiF_{2(c)} + NiF_{6(solv)}^{2-} \qquad (4)$$

Electron transfer within the Ni(III)$F_3$, yielding Ni(II)Ni(IV) $F_6$, probably provides the basis for this conversion.

XRDP of the $K_2NiF_6$ and $Cs_2NiF_6$ products in these syntheses showed that they were identical to the products of the higher temperature syntheses, each having the cubic antifluorite structure previously reported (W. Klemm, and E. Huss, *Z. anorg. Chem.*, 258, 1949, 221 and H. Bode, and E. Voss, *Z. anorg. Chem.*, 286, 1956, 136, which is herein incorporated by reference). The $Na_2NiF_6$ made by the subject technique was always contaminated with sodium bifluoride and an XRDP confirmed that mixture, the pattern of $Na_2NiF_6$ being that given by Fleischer and Hoppe(T. Fleischer, and R. Hoppe, *Z. anorg. Chem.*, 490, 1982, which is herein incorporated by reference). No attempt was made to separate this mixture. On the other hand the separation of $Li_2NiF_6$ from its accompanying LiF and $LiHF_2$ was easily achieved by washing out the easily soluble (aHF) lithium hydrofluoride (solubility: 4 mol/Kg aHF, at 0° C.) from the slightly soluble $Li_2NiF_6$ (solubility: 0.027 mol/Kg aHF). XRDP of the latter (Table 4) showed it to have a primitive hexagonal unit cell indicative of the $Na_2SiF_6$—type structure (C. Cipriani, *Rend. Soc. Mineral. Ital.*, 11, 1955, 58 and A. Zalkin, J. D. Forrester, and D. H. Templeton, *Acta Cryst.*, 17, 1964, 1408, which are herein incorporated by reference). The small formula unit volume (91.9 Å³) is the smallest for any known $A_2MF_6$ structure except $Li_2SiF_6$ (88.9 Å³). This is consistent with the low-spin $d^6$ configuration of Ni(IV) and the high effective nuclear charge of Ni(IV) in that configuration (G. Lucier, C. Shen, W. J. Casteel, Jr., L. Chacón, and N. Bartlett, *J. Fluor. Chem.*, 72, 1995, 157).

Additionally, concerning the fluorination of cationic species, it is disclosed in detail that $NiF_6^{2-}$ efficiently fluorinates $[N(CH_3)_4]^+$ forming a range of fluorinated cations the most highly fluorinated of which is $[N(CF_2H)_3CH_3]^+$, a novel species. R-$NiF_3$ with $[N(CH_3)_4]^+$ is less effective in fluorinated-cation formation, producing more highly fluorinated molecular species such as $N(CF_3)_3$. Qualitatively the products of the fluorination of $[HN(CH_3)_3]^+$ by either R-$NiF_3$ or $NiF_6^{2-}$ resemble those of the Simons Process. $NiF_6^{2-}$ is more effective than R-$NiF_3$ in adding fluorine to the multiple bond in $CH_3CN$, yielding predominantly $CF_3CF_2NF_2$; R-$NiF_3$ gives mainly $CF_3CN$, as in the Simons Process. $NiF_2$ is converted at ~20° C., in basic aHF by fluorine in visible or UV light, to $NiF_6^{2-}$.

Because $NiF_4$ (under aHF) loses ½ $F_2$ above –60° C. it remains poorly characterized but the trifluoride has been prepared (B. Zemva, K. Lutar, L. Chacón, M. Fele-Beuermann, J. Allman, C. Shen, and N. Bartlett, *J. Am. Chem. Soc.*, 117, 1995, 10025) in three forms: approximately hexagonal-close-packed rhombohedral (R-$NiF_3$), hexagonal tungsten bronze (H-$NiF_3$) and pyrochlore (P-$NiF_3$) the last two having small $K^+$ content (and corresponding Ni(II) incorporation). The $NiF_3$ forms can be kept indefinitely at approximately 20° C. in a dry atmosphere but all lose fluorine slowly in aHF at ambient temperature.

As indicated above, Applicant Bartlett recognized that $NiF_3$ and $NiF_4$ might have relevance to Simons-Process chemistry. In addition, since even $NiF_3$ was found (B. Zemva, K. Lutar, L. Chacón, M. Fele-Beuermann, J. Allman, C. Shen, and N. Bartlett, *J. Am. Chem. Soc.*, 117, 1995, 10025) to be thermodynamically unstable with respect to $NiF_2$ and $F_2$ it was evident that the new nickel fluorides would be far superior, as oxidative fluorinators, than cobalt trifluoride, which has long been used (M. Stacey, and J. C. Tatlow, *Adv. Fluorine Chem.*, 1, 1960, 166 and references cited therein and R. E. Banks and J. C. Tatlow, *Fluorine, the First Hundred Years*, ed. R. E. Banks, D. W. A. Sharpe and J. C. Tatlow, Elsevier, 1986, p. 267–337 and references cited therein, which is herein incorporated by reference) in the preparation of the perfluoro organic compounds. The collaborative work with the group of Chambers, quickly demonstrated (N. Bartlett, R. D. Chambers, A. J. Roche, R. C. H. Spink, L. Chacón, and J. M. Whalen, *Chem. Commun.*, 1996, 1049, which is herein incorporated by reference) the quasi-Simons-Process chemistry of $NiF_3$. As in the Simons Process, a substituted perhydro cyclic ether was efficiently fluorinated by R-$NiF_3$. Either this, or $NiF_4$ generated in situ, also quantitatively converted a cyclohexane derivative containing perfluoropropenyl substituents (to enhance solubility in aHF) to its perfluorinated relative (the substituents being oxidized to perfluoropropanyl). Perhaps the most important aspect of that fluorination was the complete replacement of all H on carbon, even H on a tertiary carbon linked to perfluoro carbon groups, without any detected carbon to carbon bond scission having occurred. The most dramatic fluorination, carried out using $NiF_4$ generated in situ, was the clean room temperature conversion of the adamantane derivative 3 (see Scheme 3, above) to its perfluoro derivative 3a (see Scheme 3, above), no other products being detected.

Because $NiF_3$ (in all its forms) disproportionates (B. Zemva, K. Lutar, L. Chacón, M. Fele-Beuermann, J.

Allman, C. Shen, and N. Bartlett, *J. Am. Chem. Soc.*, 117, 1995, 10025) with basic fluorides in aHF:

$$2NiF_3 + 2F^- \rightarrow NiF_2 + NiF_6^{2-} \qquad (5)$$

it seemed likely, that under more basic Simons-Process conditions, that $NiF_6^{2-}$ could have a role in that chemistry. Since Stein et al. (L. Stein, J. M. Neil, and G. R. Alms, *Inorg. Chem.*, 8, 1969, 2472) observed both this and $NiF_6^{3-}$ in the vicinity of a nickel anode, it is also plausible to assume that the latter could also have a role in that chemistry. Accordingly, the Applicants studied the salts of $NiF_6^{2-}$ and $NiF_6^{3-}$ for fluorination capabilities. The salt $K_2NiF_6$ in aHF was even included in the early investigations (N. Bartlett, R. D. Chambers, A. J. Roche, R. C. H. Spink, L. Chacón, and J. M. Whalen, *Chem. Commun.*, 1996, 1049, which is herein incorporated by reference) where it proved to be effective in oxidizing unsaturated systems. It was also efficient in substituting F for H, but not at tertiary carbon already linked to three perfluoro-carbon centers, for that task, R-$NiF_3$ or $NiF_4$ was needed.

In Applicants' investigations each of the reagents, $NiF_3$, $NiF_4$, $NiF_6^{2-}$ or $NiF_6^{3-}$ has been used in aHF, sometimes at temperatures as low as −78° C. Emphasis has been on their interaction with acetonitrile, trimethylamine and the tetramethyl ammonium cation, these being chosen for their relative simplicity, and relationship to systems previously studied in the Simons Process.

Specifically, Fluorination of $CH_3CN$

Acetonitrile was chosen as a substrate molecule for the oxidative fluorinations with the high-valent nickel fluorides because it has been investigated (N. Watanabe, and M. Haruta, Kenkyu, Hokoku Asahi Garasu Kogyo Gijutsu Shoreikai, 27, 1975/6, 1/10 and 25, 1974, 11/20, which is herein incorporated by reference) in the Simons Process, is a commonly used solvent for strong oxidizers (A. A. Emara, and G. J. Schrobilgen, *J. Chem. Soc., Chem. Commun.*, 1987, 1644, which is herein incorporated by reference) (such as $XeF_2$) and can provide a wide range of fluorinated products (from $FCH_2CN$ to $CF_3CF_2NF_2$). Table 1 summarizes the findings in its interaction, in aHF, at various temperatures below ambient, with R-$NiF_3$, $K_2NiF_6$ and $K_3NiF_6$ and compares the detected products with those of the Simons Process.

TABLE 1

Fluorinations of $CH_3CN$ with R-$NiF_3$, $K_2NiF_6$, $K_3NiF_6$, and Simons Process.

| | Fluorination Methods in aHF Solvent | | | |
|---|---|---|---|---|
| Reaction Products | R-$NiF_3$[a] | $K_2NiF_6$[b] | $K_3NiF_6$[c] | Simons Process[d] |
| | Relative Distribution | | | |
| $CF_3CN$ | 100 | 8 | 100 | 100 |
| $CF_3CF_2NF_2$ | 5 | 100 | 8 | 20 |
| $C_2F_6$ | 12 | 25 | <1 | |
| $CF_4$ | <4 | <3 | n.o. | |
| $NF_3$ | <4 | <3 | <1 | |

[a] Molar ratio R-$NiF_3$:$CH_3CN$ = 6.4:1.0 (−25 to −20° C. for 3 h; → RT over 9 h).
[b] Molar ratio $K_2NiF_6$:$CH_3CN$ = 5.5:1.0 (−45 to −30° C. for 3 h; → RT over 9 h).
[c] Molar ratio $K_3NiF_6$:$CH_3CN$ = 11.0:1.0 (−55 to −30° C. for 14 h; → RT over 4 h).
[d] Electrochemical fluorination of $CH_3CN$ in aHF solvent, ref (16).
n.o.: not observed The R-$NiF_3$ products are close to those observed in the Simons Process, the major one being $CF_3CN$. This powerful oxidizer also results in appreciable C—N and C—C bond cleavage as represented by the $C_2F_6$, $CF_4$ and $NF_3$ formation. Such cleavage is significantly less with the $K_3NiF_6$ reagent and the overall yield of $CF_3CN$ higher than with R-$NiF_3$ or the Simons Process. The $NiF_6^{3-}$ species is largely solvolysed under the conditions used however.

The aHF solvolysis of $NiF_6^{3-}$, rapidly produces a dark red precipitate which resembles the $NiF_x$ (2<x<3) reported by Zemva et al. (B. Zemva, K. Lutar, L. Chacón, M. Fele-Beuermann, J. Allman, C. Shen, and N. Bartlett, *J. Am. Chem. Soc.*, 117, 1995, 10025). In addition, $NiF_6^{2-}$, indicated by its characteristic ruby red solution color, is generated by Ni(III) disproportionation, but if we represent $NiF_x$ as $NiF_{2.5}$ (which the earlier studies (B. Zemva, K. Lutar, L. Chacón, M. Fele-Beuermann, J. Allman, C. Shen, and N. Bartlett, *J. Am. Chem. Soc.*, 117, 1995, 10025) suggest) the ratio of $NiF_{2.5}$ to $NiF_6^{2-}$ derived from the $NiF_6^{3-}$ should be 2:1. The fluorination of $CH_3CN$ certainly involves both. The mildness of the fluorination as represented by the small fraction of bond scission products probably arises from the low resultant concentration of the $NiF_6^{2-}$ species and the less aggressive oxidizing properties of the $NiF_x$. This finding indicates that an anode coating with composition below $NiF_3$ could still be an effective oxidizer and fluorinator. As is seen, the more concentrated solutions of $NiF_6^{2-}$ give a different product distribution.

The high yield of $CF_3CF_2NF_2$ in the interaction of $CH_3CN$ with $NiF_6^{2-}$ reveals that this reagent is especially effective in oxidative addition of fluorine to the —C≡N π-bond system. Of course the high solubility of the $NiF_6^{2-}$ salts in aHF ensures that the dissolved substrate molecule always has $NiF_6^{2-}$ nearby as the fluorination proceeds. It is not yet known if $NiF_6^{2-}$ efficiently converts $CF_3CN$ to $CF_3CF_2NF_2$ but it is likely to do so. It is also possible that the less soluble salt $Li_2NiF_6$ could provide for a more controlled generation of $CF_3CN$, the $CF_3CF_2NF_2$ production being minimized by limiting the oxidant molarity to that of the $CH_3CN$ to 3:1.

Table 2 compares the products of the fluorination of $[HN(CH_3)_3]^+$ at temperatures well below ambient, with R-$NiF_3$ $K_2$ $NiF_6$ and by the Simons Process (H. Burger, H. Niepel, G. Pawelke, H. J. Frohn, and P. Sartori, *J. Fluorine Chem.*, 15, 1980, 231, which is herein incorporated by reference). In the case of R-$NiF_3$, there is evidence for extensive C—C and C—N bond scission associated with the high product concentrations of $CF_4$, $CHF_3$ and $C_2F_6$. This consumed much of the $NiF_3$ oxidizer, the quantity of which was limited to that needed to quantitatively convert $N(CH_3)_3$ to $N(CF_3)_3$. This accounts for the presence of $N(CF_3)_2$ ($CHF_2$) and $N(CF_3)(CHF_2)_2$ in the products. $K_2NiF_6$ caused much less bond scission, as expected for this less potent oxidizer, and it is highly probable that the major product (as in the Simons Process) would have been $N(CF_3)_3$ if more $K_2NiF_6$ had been used than here, where the sixteen oxidizing equivalents, per mole of $N(CH_3)_3$, could at best have generated pure $N(CF_3)_2(CHF_2)$ alone. That the latter was the major observed product, hints that by controlling the quantity and concentration of the $NiF_6^{2-}$ it may be possible to emphasize a particular narrow product-composition range.

TABLE 2

Comparison of Fluorination Products of $HN(CH_3)_3^+$.

| | Fluorination Methods in aHF Solvent | | |
|---|---|---|---|
| Reaction Products | R-NiF$_3$[a] | K$_2$NiF$_6$[b] | Simons Process[c] |
| | Relative Distribution | | |
| N(CF$_3$)$_3$ | 84 | 58 | 100 |
| N(CF$_3$)$_2$(CHF$_2$) | 61 | 100 | 20 |
| N(CF$_3$)(CHF$_2$)$_2$ | 100 | 31 | 5 |
| N(CHF$_2$)$_3$ | n.o. | n.o. | 1 |
| NF$_3$ | obs. | n.o. | obs. |
| CHF$_3$ | 60 | 10 | obs. |
| CF$_4$ | 70 | n.o. | obs. |
| C$_2$F$_6$ | 19 | n.o. | obs. |

[a] Molar ratio R-NiF$_3$:HN(CH$_3$)$_3^+$ = 18.7:1.0.
[b] Molar ratio K$_2$NiF$_6$:HN(CH$_3$)$_3^+$ = 8.0:1.0.
[c] Electrochemical fluorination of HN(CH$_3$)$_3^+$ in aHF solvent, ref (18).
n.o.: not observed
obs.: observed, but not measured quantitatively Dimitrov et al. (A. Dimitrov, W. Radeck, St. Rüdiger, and O. Bechstein, *J. Fluorine Chem.*, 60, 1993, 57, which is herein incorporated by reference) have reported their findings on the electrochemical fluorination of a variety of a tetraalkyl ammonium species, but not [N(CH$_3$)$_4$]$^+$. Fluorinated cationic species were not reported in their products, which were always fluorinated alkyl amines. In our studies, R-NiF$_3$ with [N(CH$_3$)$_4$]$^+$ in aHF as the hydrofluoride or fluoroborate, the dominant product was N(CF$_3$)$_3$ accompanied by smaller quantities of N(CF$_3$)$_2$(CHF$_2$), N(CF$_3$)(CHF$_2$)$_2$ and N(CHF$_2$)$_3$, there being much CF$_4$ and CHF$_3$ also. $^{19}$F NMR spectroscopy not only provided the evidence for these molecular species (which were removed with the HF as volatiles) but also revealed the presence of a highly fluorinated cationic species, present in low concentration. This was detected initially by the $^{19}$F resonance attributable to (CHF$_2$) centered at −108.8 ppm relative to CFCl$_3$. Although this was never generated in high yield using R-NiF$_3$, it could be made as the major product using K$_2$NiF$_6$ as the oxidizer. Indeed NiF$_6^{2-}$ appears to be especially effective in fluorinating [N(CH$_3$)$_4$]$^+$, a number of fluorinated cationic species having been detected. Emphasis in these first investigations has centered on the identification and characterization of the highest fluorine-content cation.

FIG. 1(a, b, and c) shows the CHF$_2$ region of the $^{19}$F NMR spectrum for the products from three reactions, the reactant stoichiometries for which are given in the boxes in the upper right hand corner, for each spectrum (in summary: FIG. 1a shows the products of a K$_2$NiF$_6$ interaction with N(CH$_3$)$_4^+$AsF$_6^-$ in aHF for an 8:1 ratio, respectively; FIG. 1b shows the products of a K$_2$NiF$_6$ interaction with N(CH$_3$)$_4^+$BF$_4^-$ in aHF for a 10:1 ratio, respectively; and FIG. 1c shows the products of a K$_2$NiF$_6$ interaction with N(CH$_3$)$_4^+$BF$_4^-$ in aHF for a 15:1 ratio, respectively.). In the bottom spectrum, FIG. 1c, sufficient NiF$_6^{2-}$ (30 oxidizing equivalents) is present to oxidize [N(CH$_3$)$_4$]$^+$ to [N(CF$_3$)$_4$]$^+$. The latter is not formed. There is however a strong doublet (centered at −108.8 ppm) indicative of a novel cationic species containing CHF$_2$ groups. Similar doublets (with comparable J$_{H-F}$ values), are observed, in the upper spectra, with less negative chemical shifts as the quantity of NiF$_6^{2-}$ relative to [N(CH$_3$)$_4$]$^+$ in the reactant mix is diminished. It is surmised that the less negative the chemical shift for one of these doublets, the less fluorine does the cation contain. All of the doublets shown in FIG. 1 can with confidence be attributed to vacuum stable products, and therefore to CHF$_2$ containing cations. It was concluded that the doublet at −108.8 ppm belonged to the most highly fluorinated of the cations. No cationic species containing a CF$_3$ group has yet been established although the possibility that such a cation exists has not yet been ruled out.

The unambiguous assignment of the cation with the CHF$_2$ doublet at −108.8 ppm, has been made (J. Marc Whalen, Lisa Chacón, Mark Kubinec, and Neil Bartlett, to be published, which is herein incorporated by reference), with the aid of $^1$H NMR (which shows a CH$_3$ resonance equal in intensity to the CHF$_2$ resonance), $^{19}$F-$^1$H NOESY NMR (which established the CH$_3$ and CHF$_2$ groups to be in the same ion) and proton decoupled $^{14}$N NMR (which shows the anticipated binomial septet for a nearly tetrahedral nitrogen atom directly bonded to three chemically equivalent CHF$_2$ groups.). The cation is therefore [N(CHF$_2$)$_3$ CH$_3$]$^+$.

A 15% yield of [N(CHF$_2$)$_3$ CH$_3$]$^+$ [BF$_4$]$^-$ has been realized using the appropriate quantity of oxidizer and the high solubility of the salt in aHF, even at −50° C., provides for its convenient separation from KBF$_4$ which is of negligible solubility in aHF at that temperature. The salt slowly decomposes at room temperature (rapidly at ~65° C.) as a consequence of the cation abstracting F$^-$ from the anion:

$$[N(CHF_2)_3CH_3]^+\{BF_4]^- \rightarrow N(CHF_2)_2CH_3 + CHF_3 + BF_3 \qquad (6)$$

This decomposition has been established by $^{19}$F NMR. When the BF$_4^-$ is replaced by AsF$_6^-$ by the displacement of BF$_3$ with AsF$_5$:

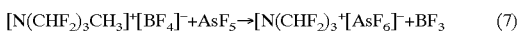

$$[N(CHF_2)_3CH_3]^+[BF_4]^- + AsF_5 \rightarrow [N(CHF_2)_3^+[AsF_6]^- + BF_3 \qquad (7)$$

the resulting salt [N(CHF$_2$)$_3$ CH$_3$]$^+$[AsF$_6$]$^-$ proves to be stable at ambient temperatures, although much less soluble in aHF than the BF$_4^-$ salt. Because of the facile decomposition of the BF$_4^-$ salt, it is highly unlikely that [N(CHF$_2$)$_4$]$^+$ could exist with that anion, but it is not yet beyond doubt that this as yet unknown cation could be stabilized by SbF$_6^-$ or even AsF$_6^-$. Prospects for [N(CF$_3$)$_4$]$^+$ prepared by methods such as these, do appear to be slightly possible.

Plainly, having appreciated the above reactions, the capability of R-NiF$_3$, in aHF, to oxidize xenon (B. Zemva, K. Lutar, L. Chacón, M. Fele-Beuermann, J. Allman, C. Shen, and N. Bartlett, *J. Am. Chem. Soc.*, 117, 1995, 10025) (ultimately giving the salt (XeF$_5$)$_2$ NiF$_6$) provides clear evidence that the oxidizer takes an electron of atomic xenon, for which the ionization potential, I, is 12.127±0.002 eV (Rhoda D. Levin and Sharon G. Lias, Ionization Potential and Appearance Potential Measurements, 1971–1981, NSRDS-NBS71, October 1982, NBS, Washington D.C. 20234, which is herein incorporated by reference). Except for CH$_4$ (I=12.6 eV) this is higher than for hydrocarbons (Rhoda D. Levin and Sharon G. Lias, Ionization Potential and Appearance Potential Measurements, 1971–1981, NSRDS-NBS71, October 1982, NBS, Washington D.C. 20234) (e.g. C$_2$H$_6$, I=12.0 eV) and even for CH$_3$CN, with I=12.20±0.01 eV. It is therefore reasonable to suppose that R-NiF$_3$ can abstract an electron, from such CH$_x$ containing species, with the same facility found with Xe. The carbohydro substrate S therefore probably undergoes first an electron oxidation, perhaps assisted by F$^-$ species placed close by. This being quickly succeeded by F$^-$ attack:

$$S \rightarrow e^- + S^+; \; S^+ + F^- \rightarrow SF \qquad (8)$$

In the majority of carbohydro molecules this probably results in HF elimination and further electron oxidation. It is plausible, with CH$_3$CN oxidation as an example, to have a reaction sequence, in which the Ni(III) centers each abstract one electron, as follows:

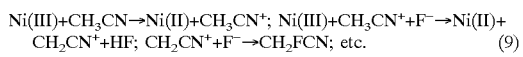

Ni(III)+CH$_3$CN→Ni(II)+CH$_3$CN$^+$; Ni(III)+CH$_3$CN$^+$+F$^-$→Ni(II)+CH$_2$CN$^+$+HF; CH$_2$CN$^+$+F$^-$→CH$_2$FCN; etc.    (9)

Since Court and Dove observed (T. L. Court, and M. F. A. Dove, *J. Chem. Soc. Chem. Commun.*, 726, 1971) have solutions of NiF$_6^{2-}$ are also able to oxidize Xe, it can be assumed that this anion is able to accomplish the same electron oxidations postulated for R-NiF$_3$. The advantages provided by aHF solutions of NiF$_6^{2-}$ are several. The oxidizer can be kept in low concentration relative to the substrate, and the degree of fluorination thereby controlled. (The aHF insoluble solids R-NiF$_3$ or NiF$_4$, seem to hold the substrate to the end of the fluorination cycle, perhaps as a consequence of the repeated formation of electron-oxidized substrate derivatives). Certain of the NiF$_6^{2-}$ salts (e.g. Li$_2$NiF$_6$) are of low solubility in aHF, which can provide for steady provision of a low concentration of oxidizer, thus providing (at least in principle) for greater product homogeneity. However, the greatest advantage provided by NiF$_6^{2-}$, rather than either R-NiF$_3$ or NiF$_4$, lies in the charge born by the species. This makes it especially valuable, as has been seen, in the fluorination of cationic species. The instability of [N(CHF$_2$)$_3$CH$_3$]$^+$ with respect of F$^-$ attack (with loss of CHF$_3$) and the inaccessibility of this cation from interaction of N(CHF$_2$)$_3$ or N(CHF$_2$)$_2$CH$_3$ with respectively CH$_3$F or CHF$_3$, points to the cation being generated by a sequence of fluorinations which always preserve a quaternary ammonium cation, [C$_4$N]$^+$. It should also be recognized that the NiF$_6^{2-}$ ion carries two oxidizing equivalents. Therefore each substrate NiF$_6^{2-}$ encounter provides for the replacement of one H ligand by one F ligand. If, as postulated, the first step is electron oxidation of the substrate this must be accompanied by NiF$_6^{3-}$. This anion is an even better F$^-$ donor than NiF$_6^{2-}$ and can more easily participate (as a labile anion, whereas NiF$_6^{2}$ is inert) in the F$^-$ attack on the substrate cation.

It is clear, from what has been shown, that for many purposes, salts of NiF$_6^{2-}$ represent an attractive alternative to anodic fluorination, as in the Simons Process. But, particularly for large scale application, the NiF$_6^{2-}$ salts have to be easily and cheaply available. To this end, Applicants have included the finding of simple ways of reconverting the NiF$_2$, produced from R-NiF$_3$, NiF$_4$ or NiF$_6^{2-}$ back to NiF$_6^{2-}$. This has been achieved at ambient temperatures (G. M. Lucier, J. M. Whalen, L. Chacón, and N. Bartlett, *J. Fluor., Chem.*, accepted for publication Sep. 5, 1997, which is herein incorporated by reference), using F$_2$ irradiated by visible or UV light (to generate F atoms (A. L. G. Rees, *J. Chem. Phys.*, 26, 1957, 1567, which is herein incorporated by reference)) in aHF made strongly basic with alkali fluoride. By this method it is especially straightforward to obtain high purity Li$_2$NiF$_6$. This confers the advantage that when the NiF$_6^{2-}$ salt is used in combination with BF$_3$, (to maintain overall neutrality, as the NiF$_6^{2-}$ is reduced to NiF$_2$), the other "waste" product is LiBF$_4$. Pyrolysis (L. J. Klinkenberg, *Rec. Trav. Chim.*, 56, 1937, 36, which is incorporated by reference) of recovered LiBF$_4$ can again provide the necessary LiF (for Li$_2$NiF$_6$ formation) and BF$_3$ (for the neutralization of the substrate/NiF$_6^{2-}$ mixture).

It is pointed out that even though the NiF$_6^{2-}$ containing salts presented her are generally ones having singly charged counter cations, NiF$_6^{2-}$ containing salts with doubly charged counter cations or mixed counter cations are possible and contemplated to be within the realm of this disclosure.

EXPERIMENTAL EXAMPLES

Materials aHF (Matheson) and F$_2$ were obtained and used as previously described (B. Zemva, K. Lutar, L. Chacón, M. Fele-Beuermann, J. Allman, C. Shen, and N. Bartlett, *J. Am. Chem. Soc.*, 117, 1995 10025, which is herein incorporated by reference). NiF$_2$ (Ozark-Mahoning Pennwalt, Tulsa, Okla. 74107) was fluorinated (F$_2$ pressure ~2000 torr) at ~250° C., to destroy water impurity. The alkali fluorides dried at 150° C. under vacuum, were as supplied by Allied Chemical, (B&A quality) Morristown, N.J. K$_2$NiF$_6$ (Ozark-Mahoning), K$_3$NiF$_6$ (Ozark-Mahoning), BF$_3$(Matheson) and AsF$_5$ (Matheson) were used without further purification. R-NiF$_3$ was prepared and used as previously described (B. Zemva, K. Lutar, L. Chacón, M. Fele-Beuermann, J. Allman, C. Shen, and N. Bartlett, *J. Am. Chem. Soc.*, 117, 1995, 10025). Acetonitrile (Fisher Scientific) was dried by refluxing with CaH$_2$ followed by distillation onto activated 3 Å molecular sieves. N(CH$_3$)$_4^+$X$^-$(X$^-$=BF$_4^-$, AsF$_6^-$) and HN(CH$_3$)$_3^+$BF$_4^-$ were prepared from the reactions each of N(CH$_3$)$_4^+$Cl$^-$ (Aldrich; dried in vacuum 3 d at 200° C.) and N(CH$_3$)$_3$ (Aldrich; 99% anhydrous) with BF$_3$ or AsF$_5$ in aHF, followed by removal of aHF and volatiles in vacuum, leaving white powders.

Irradiation Apparatus and Technique

A metal vacuum line as previously described (B. Zemva, R. Hagiwara, W. J. Casteel, Jr., K. Lutar, A. Jesih, and N. Bartlett, *J. Am. Chem. Soc.*, 112, 1990, 4846, which is herein incorporated by reference) provided for the distribution of gaseous reactants, but all of the preparations were carried out in all Teflon (FEP) apparatus, isolated from the metal system by a Teflon valve (B. Zemva, R. Hagiwara, W. J. Casteel, Jr., K. Lutar, A. Jesih, and N. Bartlett, *J. Am. Chem. Soc.*, 112, 1990, 4846) (with Kel-F stem and Teflon tips) closed, except in the transfer of the gases. (Severe corrosion of the metal vacuum system occurs if aHF, F$_2$ and fluoroacids are simultaneously present in it). A typical reactor was constructed in T shape (T reactor) from FEP tubing, Teflon Swagelok™ T, and Teflon valve as previously described (G. Lucier, C. Shen, W. J. Casteel, Jr., L. Chacón, and N. Bartlett, *J. Fluor. Chem.*, 72, 1995, 157). One arm of the T reactor was charged with NiF$_2$ and alkali fluoride in a DRILAB™ (Vacuum Atmosphere Corp.), aHF and F$_2$ (at from ~750 torr to ~1000 torr partial pressure) were introduced from the vacuum line, and that arm was arranged to be nearly horizontal, in order to maximize the F$_2$—liquid aHF interface. This nearly horizontal tube was either placed in strong sunlight, with a curved metal reflector behind it, or adjacent to the water-cooled jacket of a 450 watt immersion type Hanovia U.V. lamp (Ace Glass, Incorporated) and at the approximate line of focus of a cylindrical metal reflector, surrounding and parallel to the lamp. As the mixture was irradiated it was mixed by sideways flicking of the tube, by a properly placed rotating arm. Fluorine was replenished (at from ~750 torr to ~1000 torr. partial pressure) as it was consumed. To fully separate the NiF$_6^{2-}$ salt from unoxidized NiF$_2$ in all reactions, the purple-red supernatant solutions in aHF were decanted to the other limb of the T reactor, and the aHF back distilled to the reaction limb to extract solubles. Washing of aHF-insoluble NiF$_2$ was repeated as often as necessary to effect the separation.

Interaction of NiF$_2$ with most of the alkali fluorides (A=Li, Na, K, Cs) under a variety of aHF concentrations at ~20° C. gave the findings listed in Table 3, below.

TABLE 3

Conversion of $NiF_2$ to $A_2NiF_6$~20° C., in Liquid Anhydrous Hydrogen Fluoride, with Alkali Hydrofluoride (A = Li, Na, K, Cs) and Fluorine (at ~1 atmosphere partial pressure) in Ultraviolet Light or Sunlight (quantities of reagents in millimoles).

| $NiF_2$ | AF | HF | Irradiation time (hr) | $NiF_2$ to $A_2NiF_6$ Conversion (%)[a] |
|---|---|---|---|---|
| U.V. | | | | |
| 1.76 | LiF, 5.3 | 2.5 | 34 | $Li_2NiF_6$:48 |
| 0.935 | LiF, 2.37 | 118 | 46 | $Li_2NiF_6$:56 |
| 1.102 | NaF, 2.80 | 118 | 73 | $Na_2NiF_6$:71 |
| 1.4 | KF, 28.7 | 98.6 | 78 | $K_2NiF_6$:100 |
| 1.28 | NaF, 3.28 | 36.6[b] | 83 | $Na_2NiF_6$:69 |
| 1.12 | CsF, 3.01 | 36.6[b] | 83 | $Cs_2NiF_6$:60 |
| Sunlight | | | | |
| 2.7 | LiF, 14.5 | 115 | 37 | $Li_2NiF_6$:31 |
| 0.809 | LiF, 2.65 | 70 | 36 | $Li_2NiF_6$:17 |
| 0.143 | CsF, 2.32 | 80 | 20 | $Cs_2NiF_6$:43 |

[a]Unreacted $NiF_2$ (insoluble in aHF) and aHF-soluble components (alkali hydrofluoride and alkali salts of $NiF_6^{2-}$) were separated by decantation and washing, followed by removal of the aHF in vacuum. Percent conversion was based on the weight of $NiF_2$ consumed.
[b]Irradiation of the $NiF_2$/AF/aHF mixture necessarily results in a decrease in the fluoro-basicity of the solution as $F(HF)_x^-$ is converted to $NiF_6^{2-}$ + 2x HF. In these two experiments, a solid hydrofluoride in equilibrium with its saturated aHF solution, placed in the non-irradiated side arm, took up aHF from the irradiated mixture as the quantity of $F(HF)_x^-$ in that mixture decreased.

The conversion to $NiF_6^{2-}$ was found to be most effective (row 4) with a saturated solution of potassium hydrofluoride in aHF and a large excess of alkali over $NiF_2$. More concentrated alkali fluoride solutions always provided for quicker, more efficient, fluorination.

Much could be done to improve the irradiation effectiveness, thereby reducing the reaction time for high conversion rate, but it is already evident from the findings listed in the Table 3 that high conversion rates of $NiF_2$ to $NiF_6^{2-}$ can be achieved at or below room temperature. The quantitative conversion, attained with a high ratio of potassium fluoride to $NiF_2$ and HF (row four in Table 3, above), is achieved with the inconvenience of having a large excess of fluorobase, which must eventually be neutralized with acid or otherwise separated from the $K_2NiF_6$. When the ratio of AF to $NiF_2$ is closer to the value required (two moles AF to one of $NiF_2$) for $A_2NiF_6$ formation, the highest yield, per unit of time, is achieved using lithium fluoride as the base. The relatively low solubility, in aHF, of $Li_2NiF_6$ (relative to the other $A_2NiF_6$ salts) probably contributes to this higher efficiency.

High Purity $Li_2NiF_6$

There is no previous report of $Li_2NiF_6$. The highest oxidation-state lithium hexafluoronickelate, is $Li_3Ni(III)F_6$, made by Hagenmüller and his coworkers (J. Grannec, L. Lozano, P. Sorbe, J. Portier, P. Hagenmüller, *J. Fluor. Chem.*, 6, 1975, 267–274, which is herein incorporated by reference) at 500° C. and 70 atm. $F_2$ pressure.

Since $Li_2NiF_6$ is of relatively low solubility in aHF at 0° C. (solubility: 0.50 g/100 g aHF) the mixture, with excess lithium fluoride, produced from the $NiF_2/F_2$(U.V.)/LiF/aHF synthesis (see above in Table 3, row 1) was freed of the LiF by reducing the aHF until the solution was saturated in LiF, the bulk of the $Li_2NiF_6$ having crystallized. The LiF saturated aHF was decanted to the other limb of the T reactor (that containing the $NiF_2$ residue) and the aHF back distilled to the $Li_2NiF_6$ for washing and decantation, four times. The $Li_2NiF_6$, a dark purple-red solid, was dried in vacuum at ~20° C. ($Li_2NiF_6$ is a preferred alkali salt for $NiF_3$ and $NiF_4$ preparation since salts of the common fluoro acids (e.g. $LiBF_4$, $LiAsF_6$, $LiSbF_6$) are commonly more soluble in aHF than those of other alkalis and thus can be more easily washed free of nickel fluorides.)

The X-Ray diffraction powder photographs (XRDP) for $Li_2NiF_6$ showed no LiF, nor $LiHF_2$ impurity and the pattern was fully indexed as given in Table 4, below. XRDP were routinely obtained with $CuK\alpha$(Ni filtered) radiation on each solid, packed as a powder in thin walled quartz capillaries (B. Zemva, K. Lutar, L. Chacón, M. Fele-Beuermann, J. Allman, C. Shen, and N. Bartlett, *J. Am. Chem. Soc.*, 117, 1995 10025).

TABLE 4

X-Ray Powder Diffraction Data (Cu $K\alpha$ radiation, Ni filter) for $Li_2NiF_6$ (Hexagonal unit cell: $a_o$ = 8.321(4), $c_o$ = 4.598(2)Å, V = 275.7(1)Å$^3$, z = 3)

| | $1/d^2_{hkl} \times 10^4$ | | | | |
|---|---|---|---|---|---|
| I/Io obs. | obs. | Calc. | h | K | l |
| Vvw | 480 | 473 | 0 | 0 | 1 |
| Vvs | 578 | 578 | 1 | 1 | 0 |
| Ms* | 664 | 666 | 1 | 0 | 1 |
| W | 1053 | 1051 | 1 | 1 | 1 |
| M* | 1245 | 1245 | 2 | 0 | 1 |
| W* | 1811 | 1824 | 2 | 1 | 1 |
| W | 1892 | 1891 | 0 | 0 | 2 |
| Vvs | 2205 | 2206 | 3 | 0 | 1 |
| Vw | 2309 | 2311 | 2 | 2 | 0 |
| W | 2473 | 2469 | 1 | 1 | 2 |
| Vs | 3632 | 3624 | 3 | 0 | 2 |
| M | 4045 | 4044 | 4 | 1 | 0 |
| Vvs | 4206 | 4202 | 2 | 2 | 2 |
| W | 4519 | 4517 | 4 | 1 | 1 |
| S | 5204 | 5200 | 3 | 3 | 0 |
| Vvw* | 5608 | 5605 | 2 | 1 | 3 |
| Ms | 5937 | 5935 | 4 | 1 | 2 |
| M | 5970 | 5987 | 3 | 0 | 3 |
| Vw | 7401 | 7405 | 6 | 0 | 1 |
| W | 7500 | 7511 | 5 | 2 | 0 |
| Vw | 7547 | 7563 | 0 | 0 | 4 |
| Vvw | 8148 | 8141 | 1 | 1 | 4 |
| Mw | 8820 | 8824 | 6 | 0 | 2 |
| Vw | 9236 | 9244 | 4 | 4 | 0 |
| Vvw | 9878 | 9874 | 2 | 2 | 4 |
| Vvw | 11183 | 11187 | 6 | 0 | 3 |
| Vw | 11611 | 11607 | 4 | 1 | 4 |
| Vw | 12612 | 12606 | 6 | 3 | 1 |
| W | 12765 | 12763 | 3 | 3 | 4 |
| W | 12859 | 12868 | 7 | 1 | 2 |
| M | 14025 | 14024 | 6 | 3 | 2 |
| W | 15080 | 15074 | 5 | 2 | 4 |
| Vvw | 15599 | 15599 | 9 | 0 | 0 |
| Vw | 16322 | 16334 | 5 | 5 | 2 |

*With the omission of these broad lines the data are indexed on the formula unit cell (z = 1) with $a_o$ = 4.804(2), $c_o$ = 4.598(2)Å.

Apparatus for Fluorination

All experiments were conducted under rigorously anhydrous conditions, using reaction vessels constructed from lengths of FEP tubing, which were closed at one end by heating the end in a Bunsen flame until clear and soft then crimped to give an air-tight seal. The FEP tubes (⅜", ¼" or 4 mm o.d.), which serve as separate chambers of a reactor, were connected through a Swagelok™ Teflon T-connector equipped with Teflon ferrules to provide compression seals. Each reactor was equipped with a valve comprised of a Teflon body with Kel-F stem and Teflon tip. On a steel vacuum system, reactors were passivated with 2 atm. $F_2$ gas, and then evacuated. Solid reagents were loaded into the reactors in an argon atmosphere DRILAB™ (Vacuum Atmosphere Corp.). aHF, $BF_3$ and $AsF_5$ were vacuum condensed into the reactors at −196° C. The reactions were conducted in a aHF solvent, and were deemed to be complete when the reactor contained a tan or yellow solid ($NiF_2$; confirmed by X-ray diffraction of the dry powder in a quartz capillary). The aHF soluble products were sampled by decanting a portion of the solution into an attached 4 mm o.d. FEP tube which was then cooled to −196° C. and sealed and separated from the reactor. The products were then identified by $^{19}F$, $^{1}H$, $^{13}C$ and $^{14}N$ NMR spectroscopy, using neat external $CFCl_3(^{19}F)$, $Si(CH_3)_4(^{1}H, ^{13}C)$ and $CH_3NO_2$ ($^{14}N$) as references (positive chemical shifts are to high frequency of the reference compound) at 22° C.

Acetonitrile Fluorinations.

Slurries or solutions of nickel fluoride in ca. 0.4 ml aHF were cooled to −196° C. and $CH_3CN$ was vacuum condensed onto the frozen mixtures. Reaction mixtures were warmed to liquefy the aHF and stirred. Typical reactions: $R-NiF_3$ (1.48 mmol) and $CH_3CN$ (0.23 mmol) in aHF were warmed from −25° C. to 22° C. over 12 h. $K_2NiF_6$(0.82 mmol) and $CH_3CN$ (0.15 mmol) in aHF were warmed from −45° C. to 22° C. over 12 h. $K_3NiF_6$ (1.65 mmol) and $CH_3CN$ (0.15 mmol) in aHF were warmed from −55° C. to 22° C. over 18 h.

$HN(CH_3)_3^+BF_4^-$ Fluorinations, $K_2NiF_6$:

A −40° C. solution of $K_2NiF_6$ (5.56 mmol) in 2 mL aHF was added dropwise to a stirred −40° C. solution of $HN(CH_3)_3^+BF_4^-$ (0.70 mmol) in 2 mL aHF over 1 h., followed by warming to 3° C. over 16 h. $R-NiF_3$; An FEP cup containing $HN(CH_3)_3^+BF_4^-$ (0.19 mmol) was placed on top of $R-NiF_3$ (3.54 mmol). Liquid aHF (2 mL) was condensed onto the solids at −45° C., until the reagents were immersed, without stirring, followed by warming to −10° C. over 16 h. Then, with stirring, the reactor was warmed to 3° C. over 19 h.

$N(CH_3)_4^+X^-$ Fluorinations, $R-NiF_3$:

An FEP cup containing $N(CH_3)_4^+AsF_6^-$ (0.15 mmol) was placed on top of $R-NiF_3$ (2.76 mmol). Liquid aHF (2 mL) was condensed onto the solids at −40° C., until the reagents were immersed, without stirring, followed by warming to 0° C. over 22 h; then stirred for 24 h at 0° C. $K_2NiF_6$; $_a$ −45° C. slurry of $K_2NiF_6$ (86.2 mmol) in 25 mL aHF was added to a stirred −45° C. solution of $N(CH_3)_4^+BF_4^-$ (6.0 mmol) in 11 mL aHF over 1 h., resulting in a tan solid ($NiF_2$) and a colorless solution. At 0° C. the supernatant was decanted away, and KF in solution was converted to $KBF_4$ by reaction with 1500 Torr $BF_3$ with stirring, until no more $BF_3$ was consumed. The $KBF_4$ largely precipitated upon cooling to −60° C., and the aHF solution was decanted away. Removal of the aHF and volatiles in vacuum at 0° C. resulted in the isolation of a white powder, consisting of $[N(CHF_2)_3CH_3]^+BF_4^-$ and some $KBF_4$. $^{19}F$ NMR of the volatiles in aHF indicated the presence of $N(CF)_3$, $NF_3$, and $CF_4$. Yield $[N(CHF_2)_3CH]^+BF_4^-$, 15.0%. NMR data in aHF: $\delta(^{19}F)$=− 108.8 ($CHF_2$), −153.6 ($BF_4^-$) ppm; $\delta(^{1}H)$=7.17 ($CHF_2$), 3.54 ($CH_3$) ppm; $\delta(^{14}N)$=−265.7 ppm; $\delta(^{13}C)$=114.3 ($CHF_2$), 34.2 (CH3) ppm; $^{1}J(^{13}C-^{19}F)$=288, $^{2}J(^{14}N-^{19}F)$=8, $^{2}J(^{19}F-^{1}H)$=56, $^{1}J(^{13}C-^{1}H)$=152 Hz.

The invention has now been explained with reference to specific embodiments. Other embodiments will be suggested to those of ordinary skill in the appropriate art upon review of the present specification.

Although the foregoing invention has been described in some detail by way of illustration and example for purposes of clarity of understanding, it will be obvious that certain changes and modifications may be practiced within the scope of the appended claims.

What is claimed is:

1. A method for fluorinating a carbon compound utilizing a fluorine containing species as a fluorination agent, comprising the steps of:

a) selecting the carbon compound to undergo fluorination;
   b) choosing the fluorination agent from a group consisting of thermodynamically unstable metal fluorides and salts thereof, wherein said metal is nickel; and
   c) reacting said selected organic compound and said chosen fluorine containing species in a reaction vessel for a desired reaction time period.

2. A fluorination method according to claim 1, wherein said fluorination utilizes liquid anhydrous hydrogen fluoride as a solvent.

3. A fluorination method according to claim 1, wherein said contacting occurs at room temperature of less.

4. A fluorination method according to claim 1, wherein the organic compound contains at least a hydrogen and said hydrogen is replaced during the fluorination by a fluorine.

5. A fluorination method according to claim 1, wherein the organic compound is selected from a group consisting of saturated and unsaturated hydrocarbons, ethers, ketones, alcohols, esters, nitriles, and isonitriles.

6. A fluorination method according to claim 1, wherein said thermodynamically unstable metal fluorides are nickel fluorides selected from a group consisting of $NiF_3$ and $NiF_4$ and said salts thereof from a group consisting of $NiF_6^{2-}$ and $NiF_6^{3-}$.

7. A method for fluorinating an organic compound having at least a hydrogen to produce a derivative organic compound having said hydrogen replaced by a fluorine utilizing a fluorination agent selected from a group consisting of $NiF_3$, $NiF_4$, $NiF_6^{2-}$, and $NiF_6^{3-}$, comprising the steps of:

a) selecting the organic compound to undergo fluorination;
   b) choosing the fluorination agent; and
   c) reacting said selected organic compound and said chosen fluorination agent in a reaction vessel at approximately room temperature or less for a desired reaction time period.

8. A fluorination method according to claim 7, wherein said fluorination utilizes liquid anhydrous hydrogen fluoride as a solvent.

9. A method for fluorinating a perhydro organic compound to produce a perfluoro organic compound derivative utilizing a fluorination agent selected from a group consisting of $NiF_3$, $NiF_4$, $NiF_6^{2-}$, and $NiF_6^{3-}$, comprising the steps of:

a) selecting the perhydro organic compound to undergo fluorination;
   b) choosing the fluorination agent from said group; and
   c) reacting said selected perhydro organic compound and said chosen fluorination agent in a reaction vessel at approximately room temperature or less for a desired reaction time period.

10. A fluorination method according to claim 9, wherein said fluorination utilizes liquid anhydrous hydrogen fluoride as a solvent.

11. A method for fluorinating an organic compound having at least a hydrogen to produce a derivative organic compound having said hydrogen replaced by a fluorine, comprising the steps of:

a) selecting the organic compound to undergo fluorination and
   b) reacting said selected organic compound with $NiF_3$ in a reaction vessel at approximately room temperature or less for a desired reaction time period.

12. A fluorination method according to claim 11, wherein said fluorination utilizes liquid anhydrous hydrogen fluoride as a solvent.

13. A method for fluorinating an organic compound having at least a hydrogen to produce a derivative organic compound having said hydrogen replaced by a fluorine, comprising the steps of:
 a) selecting the organic compound to undergo fluorination and
 b) reacting said selected organic compound with $NiF_4$ in a reaction vessel at approximately room temperature or less for a desired reaction time period.

14. A fluorination method according to claim 13, wherein said fluorination utilizes liquid anhydrous hydrogen fluoride as a solvent.

15. A method for fluorinating an organic compound having at least a hydrogen to produce a derivative organic compound having said hydrogen replaced by a fluorine, comprising the steps of:
 a) selecting the organic compound to undergo fluorination and
 b) reacting said selected organic compound with $NiF_6^{2-}$ in a reaction vessel at approximately room temperature or less for a desired reaction time period.

16. A fluorination method according to claim 15, wherein said fluorination utilizes liquid anhydrous hydrogen fluoride as a solvent.

17. A method for fluorinating an organic compound having at least a hydrogen to produce a derivative organic compound having said hydrogen replaced by a fluorine, comprising the steps of:
 a) selecting the organic compound to undergo fluorination and
 b) reacting said selected organic compound with $NiF_6^{3-}$ in a reaction vessel at approximately room temperature or less for a desired reaction time period.

18. A fluorination method according to claim 17, wherein said fluorination utilizes liquid anhydrous hydrogen fluoride as a solvent.

19. A method for fluorinating an organic compound or cationic organic compound in which either the organic compound or the cationic organic compound has at least a hydrogen to produce a derivative organic compound or derivative cationic organic compound having said hydrogen replaced by a fluorine utilizing a fluorination agent selected from a group consisting of $NiF_3$ and $NiF_6^{2-}$, comprising the steps of:
 a) selecting the organic compound or cationic organic compound to undergo fluorination;
 b) choosing the fluorination agent; and
 c) reacting said selected organic compound or cationic organic compound and said chosen fluorination agent in a reaction vessel at approximately room temperature or less for a desired reaction time period.

20. A fluorination method according to claim 19, wherein said fluorination utilizes liquid anhydrous hydrogen fluoride as a solvent.

21. A method for fluorinating a cationic organic compound having at least a hydrogen to produce a derivative cationic organic compound having said hydrogen replaced by a fluorine utilizing a fluorination agent selected from a group consisting of $NiF_3$ and $NiF_6^{2-}$, comprising the steps of:
 a) selecting the cationic organic compound to undergo fluorination;
 b) choosing the fluorination agent; and
 c) reacting said selected cationic organic compound and said chosen fluorination agent in a reaction vessel at approximately room temperature or less for a desired reaction time period.

22. A fluorination method according to claim 21, wherein said fluorination utilizes liquid anhydrous hydrogen fluoride as a solvent.

23. A method for fluorinating a cationic organic compound having at least a hydrogen to produce at least one derivative cationic organic compound having said hydrogen replaced by a fluorine utilizing a fluorination agent selected from a group consisting of $NiF_3$ and $NiF_6^{2-}$, comprising the steps of:
 a) selecting the cationic organic compound to undergo fluorination and
 b) reacting said selected cationic organic compound with $NiF_6^{2-}$ in a reaction vessel at approximately room temperature or less for a desired reaction time period.

24. A fluorination method according to claim 23, wherein said fluorination utilizes liquid anhydrous hydrogen fluoride as a solvent.

25. A method for fluorinating an organic compound having at least a hydrogen to produce a derivative organic compound having said hydrogen replaced by a fluorine from an in situ generated fluorination agent, comprising the steps of:
 a) selecting the organic compound to undergo fluorination;
 b) producing the fluorination agent, in situ, wherein said fluorination agent is $NiF_4$ generated from a reaction between $NiF_6^{2-}$ and $BF_3$; and
 c) reacting said selected organic compound and in situ produced $NiF_4$ fluorination agent in a reaction vessel at approximately room temperature or less for a desired reaction time period.

26. A fluorination method according to claim 25, wherein said fluorination utilizes liquid anhydrous hydrogen fluoride as a solvent.

* * * * *